(12) United States Patent
Wu et al.

(10) Patent No.: US 9,042,978 B2
(45) Date of Patent: May 26, 2015

(54) METHOD AND APPARATUS FOR QUANTITATIVE NERVE LOCALIZATION

(75) Inventors: Changwang Wu, Newton, MA (US); Shai Gozani, Brookline, MA (US); Xuan Kong, Acton, MA (US)

(73) Assignee: NeuroMetrix, Inc., Waltham, MA (US)

( * ) Notice: Subject to any disclaimer, the term of this patent is extended or adjusted under 35 U.S.C. 154(b) by 1154 days.

(21) Appl. No.: 12/475,152

(22) Filed: May 29, 2009

(65) Prior Publication Data

US 2009/0299214 A1     Dec. 3, 2009

Related U.S. Application Data

(63) Continuation-in-part of application No. 11/801,865, filed on May 11, 2007, now abandoned, and a continuation-in-part of application No. 12/002,039, filed on Dec. 14, 2007, now abandoned, and a continuation-in-part of application No. 12/274,759, filed on Nov. 20, 2008, now Pat. No. 8,029,313.

(60) Provisional application No. 61/130,205, filed on May 29, 2008.

(51) Int. Cl.
| | |
|---|---|
| *A61N 1/05* | (2006.01) |
| *A61B 5/04* | (2006.01) |
| *A61N 1/04* | (2006.01) |
| *A61N 1/08* | (2006.01) |
| *A61N 1/36* | (2006.01) |
| *A61N 1/372* | (2006.01) |

(52) U.S. Cl.
CPC .......... *A61B 5/04001* (2013.01); *A61N 1/0456* (2013.01); *A61N 1/0502* (2013.01); *A61N 1/08* (2013.01); *A61N 1/36021* (2013.01); *A61N 1/37211* (2013.01)

(58) Field of Classification Search
CPC ..... A61N 1/0456; A61N 1/08; A61B 5/04001
USPC .............................................. 607/2
See application file for complete search history.

(56) References Cited

U.S. PATENT DOCUMENTS

| | | | |
|---|---|---|---|
| 4,515,168 | A | 5/1985 | Chester et al. |
| 4,722,343 | A | 2/1988 | Lombardi |
| 4,902,244 | A | 2/1990 | Endo et al. |
| 4,925,402 | A | 5/1990 | Inaba et al. |
| 5,169,336 | A | 12/1992 | Taguchi |

(Continued)

OTHER PUBLICATIONS

Nilsson, Jan et al., Stimulus Artifact Compensation Using Biphasic Stimulation, Muscle & Nerve, 1988, pp. 597-602, vol. 11.

(Continued)

*Primary Examiner* — Eric D. Bertram
(74) *Attorney, Agent, or Firm* — Pandiscio & Pandiscio (57) ABSTRACT

A method for localizing a needle to a nerve, the method comprising:
using the needle to electrically stimulate the nerve, with a known current intensity, so as to evoke a nerve response;
detecting the nerve response;
analyzing the detected nerve response so as to identify at least one attribute of the same; and
confirming that the needle is in the immediate proximity of the nerve based upon known current intensity and at least one identified attribute of the detected nerve response.

83 Claims, 4 Drawing Sheets

(56) References Cited

U.S. PATENT DOCUMENTS

| | | | |
|---|---|---|---|
| 5,170,788 A | 12/1992 | Blumenfeld | |
| 5,222,164 A | 6/1993 | Bass, Sr. et al. | |
| 5,284,153 A * | 2/1994 | Raymond et al. | 600/554 |
| 5,284,154 A | 2/1994 | Raymond et al. | |
| 5,299,119 A | 3/1994 | Kraf et al. | |
| 5,588,873 A | 12/1996 | Hamai et al. | |
| 5,758,651 A | 6/1998 | Nygard et al. | |
| 5,775,331 A | 7/1998 | Raymond et al. | |
| 5,851,191 A | 12/1998 | Gozani | |
| 5,976,094 A | 11/1999 | Gozani | |
| 6,132,386 A | 10/2000 | Gozani et al. | |
| 6,146,335 A | 11/2000 | Gozani | |
| 6,208,891 B1 | 3/2001 | Flower | |
| 6,259,945 B1 | 7/2001 | Epstein et al. | |
| 6,266,558 B1 | 7/2001 | Gozani et al. | |
| 6,466,817 B1 | 10/2002 | Kaula et al. | |
| 6,533,732 B1 * | 3/2003 | Urmey | 600/554 |
| 6,535,759 B1 | 3/2003 | Epstein et al. | |
| 6,655,983 B1 | 12/2003 | Ishikawa et al. | |
| 6,890,197 B2 | 5/2005 | Liebenow | |
| 6,968,233 B1 | 11/2005 | Parry et al. | |
| 7,282,033 B2 * | 10/2007 | Urmey | 600/554 |
| 7,314,392 B2 | 1/2008 | Pharn et al. | |
| 7,384,300 B1 | 6/2008 | Salgado et al. | |
| 7,452,335 B2 | 11/2008 | Wells et al. | |
| 7,493,157 B2 | 2/2009 | Gozani et al. | |
| 7,628,761 B2 | 12/2009 | Gozani et al. | |
| 7,749,171 B2 | 7/2010 | Gozani et al. | |
| 2002/0169371 A1 | 11/2002 | Gilderdale | |
| 2003/0088185 A1 | 5/2003 | Prass | |
| 2003/0093006 A1 | 5/2003 | Wells et al. | |
| 2004/0204669 A1 | 10/2004 | Hofmann | |
| 2005/0197680 A1 | 9/2005 | DelMain et al. | |
| 2005/0261559 A1 | 11/2005 | Mumford et al. | |
| 2006/0020222 A1 | 1/2006 | Gozani et al. | |
| 2008/0051647 A1 | 2/2008 | Wu et al. | |
| 2008/0090451 A1 | 4/2008 | Feldman | |
| 2008/0281378 A1 | 11/2008 | Williams et al. | |

OTHER PUBLICATIONS

McGill, Kevin et al., On the Nature and Elimination of Stimulus Artifact in Nerve Signals Evoked and Recorded Using Surface Electrodes, IEEE Transactions on Biomedical Engineering, Feb. 1982, pp. 129-137, vol. BME-29, No. 2.

* cited by examiner

METHOD AND APPARATUS FOR QUANTITATIVE NERVE LOCALIZATION

REFERENCE TO PENDING PRIOR PATENT APPLICATIONS

This patent application is:

(i) a continuation-in-part of prior U.S. patent application Ser. No. 11/801,865, filed May 11, 2007 now abandoned by Changwang Wu et al. for NON-INVASIVE ACQUISITION OF LARGE NERVE ACTION POTENTIALS (NAPs) WITH CLOSELY SPACED SURFACE ELECTRODES AND REDUCED STIMULUS ARTIFACTS;

(ii) a continuation-in-part of prior U.S. patent application Ser. No. 12/002,039, filed Dec. 14, 2007 now abandoned by Michael Williams et al. for NEUROLOGICAL DIAGNOSTIC AND THERAPEUTIC SYSTEM UTILIZING FUNCTION-SPECIFIC MODULES;

(iii) a continuation-in-part of prior U.S. Pat. application Ser. No. 12/274,759, now U.S. Pat. No. 8,029,313, filed Nov. 20, 2008 by Charles Fendrock et al. for DISPOSABLE NEEDLE ELECTRODE WITH IDENTIFICATION, AND ALTERABLE, CONNECTOR INTERFACE; and (iv) claims benefit of prior U.S. Provisional Patent Application Ser. No. 61/130,205, filed May 29, 2008 by Changwang Wu et al. for QUANTITATIVE NERVE LOCALIZATION.

The four (4) above-identified patent applications are hereby incorporated herein by reference.

FIELD OF THE INVENTION

This invention relates to methods and apparatus for electrically stimulating a nerve using a needle and a surface electrode, detecting the nerve response, and localizing the needle to the nerve based upon the characteristics of the detected nerve response. This localization information can then be used to improve the application of regional anesthesia, to apply therapy to the nerve, etc.

BACKGROUND OF THE INVENTION

Nerve localization (NL) is a common procedure in the application of regional anesthesia and in the localized treatment of certain neuropathies. Typically, the physician passes a needle through the skin and subcutaneous tissue of the patient, and then advances the needle into close proximity to a target nerve, at which point a pharmacologically-active agent (e.g., corticosteroids, lidocaine, etc.) is delivered to the nerve.

One of the clinical challenges associated with NL is the need to position the needle within close proximity to the target nerve, but without physical contact.

Electrical nerve stimulation (NS) may be used to help guide needle movement during a NL procedure. More particularly, after the needle is inserted in the patient, an electrical stimulator delivers an electrical current through the needle that is high enough (typically a few milliamps) to stimulate the nerve so that a visible muscle contraction response (for a motor nerve) or a patient-detectable sensory response (for a sensory nerve) is obtained. The magnitude of the current is thereafter manipulated (generally decreased) as the needle is being advanced. When targeted muscle contractions are visually observed (or when sensory responses are being reported by the patient) at a low pre-determined current magnitude (typically 0.2-0.5 milliamps), it is believed that the tip of the needle is sufficiently close to the nerve for effective delivery of the pharmacologically-active agent.

While the prior art electrically-guided nerve localization procedure discussed above may be an improvement over "blind" nerve localization, it is nonetheless limited for a number of reasons.

1. The assessment of a motor response to the electrical stimulation, which is critical to judging the proximity of the needle to a target motor nerve, is based solely on a subjective visual observation of muscle contraction by the user (e.g., a physician or other healthcare provider). Quantitative and objective measures of motor response intensity (i.e., measures that do not rely on a visual impression) are not utilized in current clinical techniques. The stimulation threshold for an observable muscle contraction is higher than that of an electrically recordable response (i.e., a compound muscle action potential, also known as a CMAP) and therefore current methods are not optimally sensitive.

2. The assessment of a sensory response to the electrical stimulation, which is critical to judging the proximity of the needle to a target sensory nerve, is based solely on the report of the patient. Again, quantitative and objective measures of sensory response are not utilized in current clinical techniques. Among other things, if the patient has a diminished capability of reporting sensory response (i.e., nerve sensations, or "feeling") because of neuropathy and/or because of sedation, the utility of a conventional nerve stimulator can be highly compromised. This is because a patient's sensory nerve may respond but the patient may not be able to sense it.

3. With prior art electrically-guided nerve localization, the user (e.g., a physician) must manually adjust the stimulation current intensity (usually amplitude, but the user may also adjust duration) while trying to delicately advance the needle and observe the response. This often requires two healthcare providers to perform such a procedure.

4. With the current clinical approach, it is generally concluded that the appropriate needle approximation has been achieved when the stimulation current has been reduced to some low pre-determined current magnitude, e.g., for anesthetic or drug injection, the target current is typically 0.2-0.5 milliamps (mA). However, the target current commonly varies from case to case. Thus, there is a general lack of precision and consistency with the current clinical approach.

5. In some situations the nerve stimulator response may not provide useful information and may even provide misleading information, e.g., when the target nerve has conduction problems and the motor/sensory responses are abnormal. More particularly, patients typically do not undergo a neuropathy diagnosis prior to the NL procedure. When the nerve responses are weaker than normal, a higher stimulation current intensity is required in order to evoke the same nerve response level for the same needle-nerve proximity. In this case, when the needle is already in the desired position for injection, the stimulation current may be still higher than the pre-determined threshold (0.2-0.5 mA) that is appropriate for a healthy nerve but may not be appropriate for the nerve that has neuropathology. As a consequence, the operator may not believe that the needle is close enough to the target nerve and therefore advance the needle even further, which can result in nerve injury.

6. The nerve stimulators currently in use do not have the capability of logging data and tracking the outcome of the procedure, which can be important for both clinical and medicolegal purposes.

7. Current nerve stimulators do not have the capability of permanently storing the data.

SUMMARY OF THE INVENTION

The present invention addresses the foregoing problems associated with the prior art by providing a novel method and apparatus for localizing a needle to a target nerve based upon a quantitative nerve localization procedure. More particularly, in the present invention, the target nerve is electrically stimulated using a needle and a surface electrode, the nerve responses are detected, and the needle is localized to the nerve based upon the characteristics of the nerve responses.

In a preferred form of the invention:

(i) the target nerve is electrically stimulated using a needle and a surface electrode;

(ii) the nerve response is detected (as one or more motor and/or sensory responses), processed, quantitatively measured and displayed, with the nerve responses preferably being detected by a detector (or multiple detectors, if necessary) that is connected to the electrical stimulator by a wired or wireless connection;

(iii) the stimulus intensity is automatically controlled in accordance with the quantitative response measurement;

(iv) the proximity of the needle to the nerve is automatically verified;

(v) a neuropathy diagnosis is performed;

(vi) the acquired data is logged (e.g., in memory local to, or embedded in, the electrical stimulator) and the outcome of the NL procedure is tracked; and (vii) the acquired data is transmitted to a data server (e.g., at a remote location) and a report is created.

And in a preferred form of the invention, the novel apparatus of the present invention comprises a needle localization system which comprises a main unit (which includes a stimulator unit), a detector unit, a data hub unit, and a data storage unit. The stimulator unit applies an electrical stimulus to a nerve at a stimulation site, and the detector unit detects the nerve response at a detection site. The detector unit may be in the same housing as the main unit, or it may be in a separate housing. The detected nerve signal is transferred from the detector unit to the main unit for processing, analyzing, recording, and displaying. Alternatively, the detector unit may process and analyze the detected nerve signal, and then transfer the results to the main unit. The connection between the detector unit and the main unit may be wired or wireless. The main unit transfers the data to the data storage unit (e.g., over a telephone line, the Internet, etc.) via the data hub unit.

In a preferred form of the invention, there is provided a method for localizing a needle to a nerve, the method comprising:

using the needle to electrically stimulate the nerve, with a known current intensity, so as to evoke a nerve response;

detecting the nerve response;

analyzing the detected nerve response so as to identify at least one attribute of the same; and confirming that the needle is in the immediate proximity of the nerve based upon known current intensity and at least one identified attribute of the detected nerve response.

In another preferred form of the invention, there is provided a method for localizing a medical instrument to a nerve, the method comprising:

electrically stimulating the nerve using the medical instrument so as to evoke a nerve response;

detecting the nerve response;

analyzing the detected nerve response so as to identify at least one attribute of the same; and estimating the proximity of the medical instrument to the nerve based upon known current intensity and at least one identified attribute of the detected nerve response.

In another preferred form of the invention, there is provided a method for localizing a needle to a nerve, the method comprising:

electrically stimulating the nerve, with a known current intensity, using the needle so as to evoke a nerve response;

detecting the nerve response;

analyzing the detected nerve response so as to identify at least one attribute of the same; and estimating the proximity of the needle to the nerve based upon known current intensity and at least one identified attribute of the detected nerve response.

In another preferred form of the invention, there is provided a method for determining information about a nerve, the method comprising:

positioning sensors at a plurality of locations on a test subject;

issuing a synchronization signal to each of the sensors so as to establish a common time reference for each of the sensors;

using at least one electrode to electrically stimulate the nerve;

using the sensors to generate a plurality of nerve traces, wherein each nerve trace is indicative of the nerve response at a given location; and analyzing the plurality of nerve traces so as to determine at least one attribute for each nerve trace, and using the common time reference to place the determined attributes in proper time registration with one another.

In another preferred form of the invention, there is provided apparatus for localizing a needle to a nerve, the apparatus comprising:

an electrical stimulator connected to the needle for electrically stimulating the nerve, with a known current intensity, so as to evoke a nerve response;

at least one sensor for detecting the nerve response;

an analysis unit connected to the sensor for receiving the detected nerve response and identifying at least one attribute of the same; and a localizing unit connected to the analysis unit for confirming that the needle is in the immediate proximity of the nerve based upon known current intensity and at least one identified attribute of the detected nerve response.

In another preferred form of the invention, there is provided apparatus for localizing a medical device to a nerve, the apparatus comprising:

an electrical stimulator connected to the medical device for electrically stimulating the nerve, with a known current intensity, so as to evoke a nerve response;

at least one sensor for detecting the nerve response;

an analysis unit connected to the sensor for receiving the detected nerve response and identifying at least one attribute of the same; and a localizing unit connected to the analysis unit for confirming that the medical device is in the immediate proximity of the nerve based upon known current intensity and at least one identified attribute of the detected nerve response.

In another preferred form of the invention, there is provided apparatus for localizing a needle to a nerve, the apparatus comprising:

means for electrically stimulating the nerve, with a known current intensity, using the needle so as to evoke a nerve response;

means for detecting the nerve response;

means for analyzing the detected nerve response so as to identify at least one attribute of the same; and means for estimating the proximity of the needle to the nerve based upon known current intensity and at least one identified attribute of the detected nerve response.

In another preferred form of the invention, there is provided apparatus for determining information about a nerve, the apparatus comprising:

sensors positioned at a plurality of locations on a test subject;

means for issuing a synchronization signal to each of the sensors so as to establish a common time reference for each of the sensors;

at least one electrode for electrically stimulating the nerve;

means connected to the sensors for generating a plurality of nerve traces, wherein each nerve trace is indicative of the nerve response at a given location; and means for analyzing the plurality of nerve traces so as to determine at least one attribute for each nerve trace, and using the common time reference to place the determined attributes in proper time registration with one another.

BRIEF DESCRIPTION OF THE DRAWINGS

These and other objects and features of the present invention will be more fully disclosed or rendered obvious by the following detailed description of the preferred embodiments of the invention, which is to be read in conjunction with the accompanying drawings wherein like numbers refer to like elements, and further where.

DETAILED DESCRIPTION OF THE PREFERRED EMBODIMENTS

Figure 1:
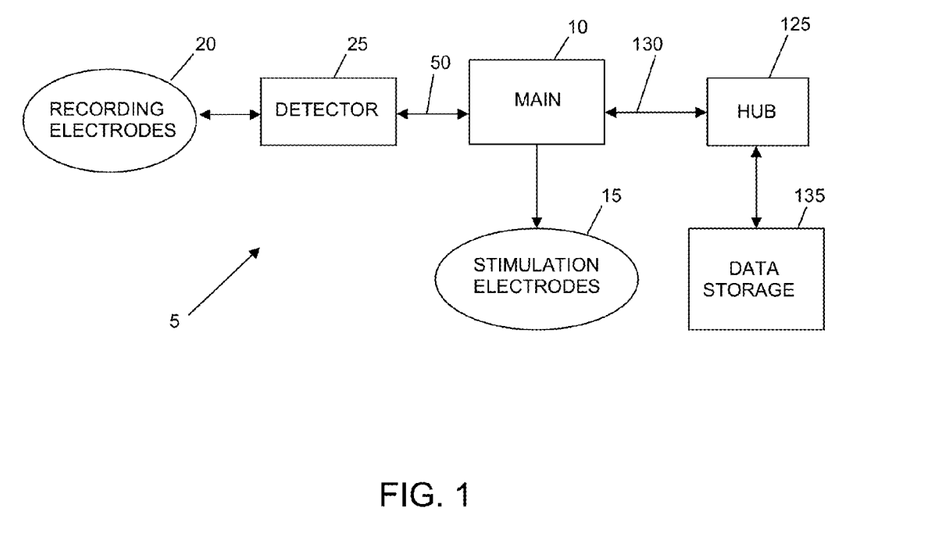
FIG. 1 is a schematic block diagram showing one preferred needle localization system formed in accordance with the present invention.

Quantitative and Objective Measurement of the Evoked Nerve Response in a Nerve Localization Procedure Looking first at FIG. 1, there is shown a needle localization system 5 for electrically stimulating a nerve of a patient (also sometimes referred to herein as the test subject) using a needle and a surface electrode, detecting the nerve response, and localizing the needle to the nerve based upon the characteristics of the detected nerve responses. In accordance with the present invention, the nerve responses detected by monitoring the muscle innervated by the nerve (in the case of a motor nerve) or by monitoring another portion of the nerve (in the case of a sensory nerve) so as to provide a nerve response trace, and then detecting variations in the nerve response trace which are indicative of nerve response (e.g., variations in the amplitude of the trace).

More particularly, needle localization system 5 generally comprises a main unit 10 for stimulating a nerve through stimulation electrodes 15 (which may include a mono-polar needle and a surface electrode, or a bi-polar needle), detecting the nerve responses through an electrode 20, and then processing, quantitatively measuring and displaying the evoked nerve responses via a detector unit 25 and main unit 10.

Figure 2:
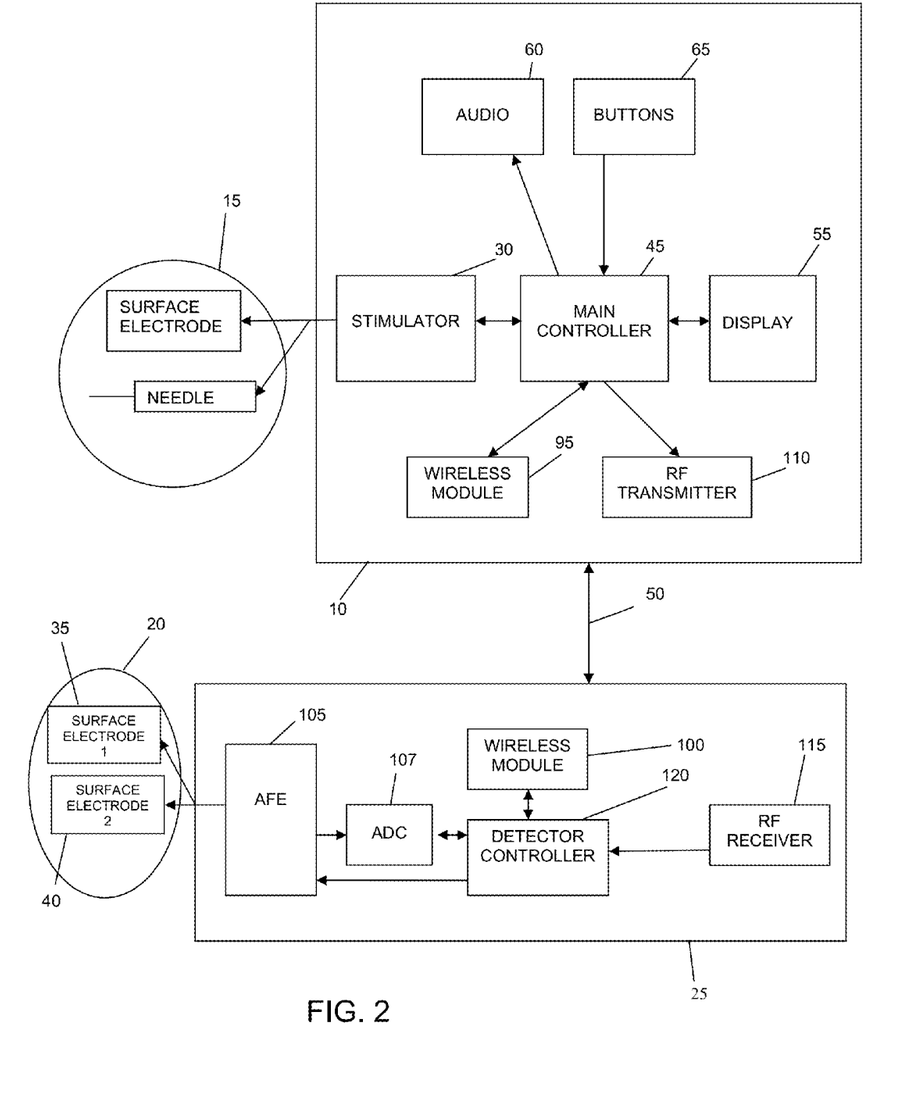
FIG. 2 is a schematic block diagram showing the main unit and the detector unit of the needle localization system shown in FIG. 1.

As seen in FIG. 2, main unit 10 comprises an adjustable, constant current stimulation circuit (also known as "the stimulator") 30 that delivers an electrical stimulus to the stimulation electrodes 15 so as to stimulate a nerve of the patient. The nerve response is detected by electrode apparatus 20 which includes a pair of surface electrodes 35, 40, preferably in conjunction with a reference surface electrode (not shown). Electrode apparatus 20 is connected to detector unit 25. A main controller 45 operates stimulator 30, and receives the detected nerve signal from detector unit 25.

The detected nerve signal (i.e., the nerve response trace) is processed and measured by the system so as to identify variations in the nerve response trace which are indicative of nerve response (e.g., amplitude variations which are indicative of nerve response). By way of example but not limitation, the nerve response may be detected by monitoring the muscle innervated by a nerve (in the case of a motor nerve) or by monitoring another portion of the nerve (in the case of a sensory nerve) so as to provide a nerve response trace, and then detecting variations in the nerve response trace which are indicative of nerve response (e.g., amplitude variations). By way of further example but not limitation, the onset of a CMAP event in a nerve response trace may be used to identify a nerve response in a motor nerve.

The detected nerve signal may be processed and measured in either detector unit 25 or in main unit 10, or both. Main unit 10 displays this nerve signal measurement and/or the detected nerve signal trace. Main controller 45 may also receive the stimulation current trace and the stimulation voltage trace from stimulator 30. The connection 50 between detector unit 25 and main unit 10 may be wired or wireless. Display 55, audio output 60 and buttons 65, as well as other optional input/output controls, permit a user to interact with the system.

Unlike prior art electrically-guided nerve localization systems, the present invention allows the user to assess the motor or sensory nerve response to the electrical stimulation based on the additional quantitative and objective measurement, and visual display, of the nerve response trace, and does not require the user to rely on a subjective visual observation of the strength of a muscle contraction (for motor nerves) or a patient report of sensation (for sensory nerves). This feature of the present invention is particularly important where the target nerve has reduced response due to neuropathy or patient sedation.

Automated Control of Stimulus Intensity Based on Quantitative Nerve Response Measurements During the stimulator-guided nerve localization procedure, as the needle-to-nerve distance (known as needle-nerve distance) decreases, the stimulation current intensity required to evoke a response decreases, and vice versa. When the stimulation current intensity is equal to, or less than, the target current (typically 0.2-0.5 mA), the needle is considered to be in the proper position to inject the pharmacologically-active agent. Prior art systems require the user to manually adjust the stimulation current intensity while advancing the needle toward the nerve. In contrast, the preferred embodiment of the present invention automatically adjusts the stimulation current intensity based on the nerve response signals. This is a major advance over the prior art.

In one preferred form of the present invention, needle localization system 5 preferably uses the following approach to automatically adjust the stimulation current intensity based on the detected nerve response signals:

(1) The user inserts the needle to a shallow depth.

(2) The system continuously delivers stimuli with increased intensity (i.e., increased current magnitude) and with a repetition rate in the 1 to 2 Hz range until an evoked nerve response is detected and displayed. This step verifies that a nerve response can be evoked.

(3) The user advances the needle toward the nerve.

(4) The system delivers a single stimulus to the patient, and detects, processes and analyzes the evoked nerve response.

(5) If the magnitude of the nerve response signal is higher than a pre-determined range, then the stimulation current intensity is decreased.

(6) If the magnitude of the nerve response signal is lower than the pre-determined range, then the stimulation current intensity is increased.

(7) Steps 4-6 are repeated until the magnitude of the nerve response signal is within the pre-determined range.

(8) If the stimulation intensity is higher than the target current (typically 0.2-0.5 mA), main unit 10 signals the user that the system is ready for the needle to be advanced closer to the nerve, and steps 3-8 are repeated.

(9) If the stimulation intensity is equal to, or lower than, the target current, main unit 10 signals the user that the needle may be in the proper position to inject the pharmacologically-active agent.

Automated Verification of Needle Location and Automated Nerve Locator

During the stimulator-guided near-nerve localization procedure as discussed above, when the target nerve response can be evoked with a stimulation current that is equal to, or lower than, the target current (e.g., typically a 0.2-0.5 mA magnitude, using a 100 μs rectangular pulse width), it is generally accepted that the needle is sufficiently close to the nerve and ready for injection. However, the appropriate target current, which is used to limit further advancement of the needle toward the nerve, and hence is used to confirm proximity of the needle to the nerve, varies from case to case, i.e., from patient to patient, nerve to nerve, etc. Therefore, it is desirable to verify the position of the needle when the target current is achieved and before injection of the pharmacologically-active agent takes place.

Figure 3:
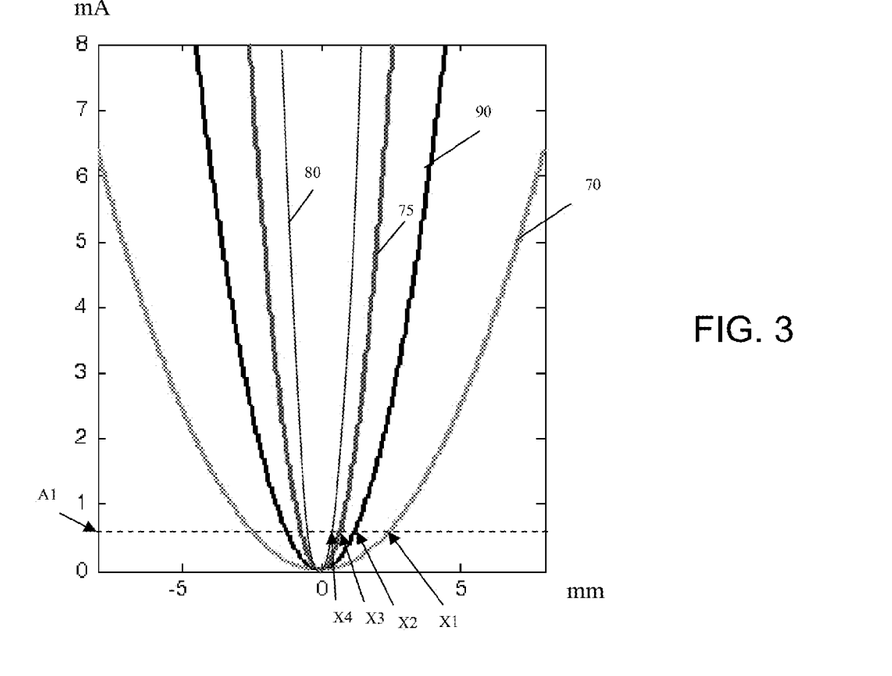
FIG. 3 is a diagram showing the relationship between (i) stimulation current magnitude and (ii) needle-nerve distance.

FIG. 3 is a diagram conceptually describing the relationship between the stimulation current magnitude and the needle-nerve distance. The horizontal coordinate represents the distance (in millimeters) from needle to nerve. The vertical coordinate represents the magnitude of the stimulation current.

With a stimulation current that has constant magnitude (e.g., a constant magnitude of A1) and a rectangular pulse waveform, when the current flows from anode to cathode (cathode stimulation), the nerve response cannot be evoked if the needle-nerve distance is outside the region of line 70 (e.g., if the needle-nerve distance is greater than X1). This is because the needle is too far from the nerve and the current intensity is not strong enough to evoke an appropriate nerve response. The nerve response can be evoked if the needle-nerve distance is less than the value defined by line 70 (e.g., if the needle-nerve distance is less than X1), but greater than the value defined by line 75 (e.g., if the needle-nerve distance is greater than X3). The nerve response may or may not be evoked if the needle-nerve distance is inside the region of line 75 (e.g., if the needle-nerve distance is less than X3). The nerve response is less likely to be evoked if the needle-nerve distance is located between line 75 and line 80 (e.g., if the needle-nerve distance is less than X3, but greater than X4), but more likely to be evoked if the distance is less than the value defined by line 80 (e.g., if the needle-nerve distance is less than X4). The area within line 75 may be referred to as a "blocked area".

The blocked area is usually created due to a strong cathode stimulus. Cathode stimulation creates a positive driving force to activate a nerve segment that is directly below the stimulus source, but negative driving force to deactivate the adjacent nerve segments. With a small stimulus, the negative driving force is usually too weak to block the activated signal propagating through the side sections. However, while the needle stimulus becomes stronger and closer to the nerve, the negative driving force is increased and it may block the activating signal propagating through the nerve's side segments. In this case, the nerve does not create a response, and the blocked area may be observed in the stimulus range. However, this blocked phenomenon is not always observable if the stimulus signal (see FIG. 4) is suddenly terminated (i.e., if the stimulus comprises a rectangular pulse waveform). The sudden disappearance of the stimulus provides an opportunity for the nerve transmembrane voltage at the aforementioned side sections to arise quickly, and this change may elicit a nerve response, which may be referred to as an "anode breakdown" phenomena. The stronger the stimulus intensity, the larger the transmembrane voltage change, and thus the more likely for the "anode breakdown" phenomenon to occur. Therefore, in order to observe a full blocked area within line 75, a stimulus signal with a gradual falling edge 85 (FIG. 4) is used to eliminate the "anode breakdown" phenomena by reducing the sudden changes of the nerve transmembrane voltage. Furthermore, it has been found that the stronger the stimulus, the longer that falling edge 85 needs to be.

With the same stimulation current intensity and rectangular pulse waveform, when the current flows from cathode to anode (anodic stimulation), the nerve response can be evoked if the needle-nerve distance is less than the value defined by line 90 (e.g., the needle-nerve distance is less than X2). The nerve response cannot be evoked if the needle-nerve distance is greater than the value defined by line 90 (e.g., greater than X2).

The present invention utilizes the foregoing to automatically verify that the needle is close to the nerve. More particularly, in one preferred form of the present invention, needle localization system 5 preferably uses the following approach to automatically verify that the needle is close to the nerve:

(1) The needle is advanced under guidance from system 5, which stimulates the nerve with stimulation current flowing from anode to cathode (cathode stimulation). This stimulation current has a rectangular pulse waveform. The current intensity is gradually reduced while the needle is moving and the nerve response has been detected. Advancement of the needle is stopped when the nerve response can be evoked by a stimulation current which has magnitude equal to, or lower than, the target current (typically 0.2-0.5 mA when the stimulation pulse width is 100 μs)

Figure 4:
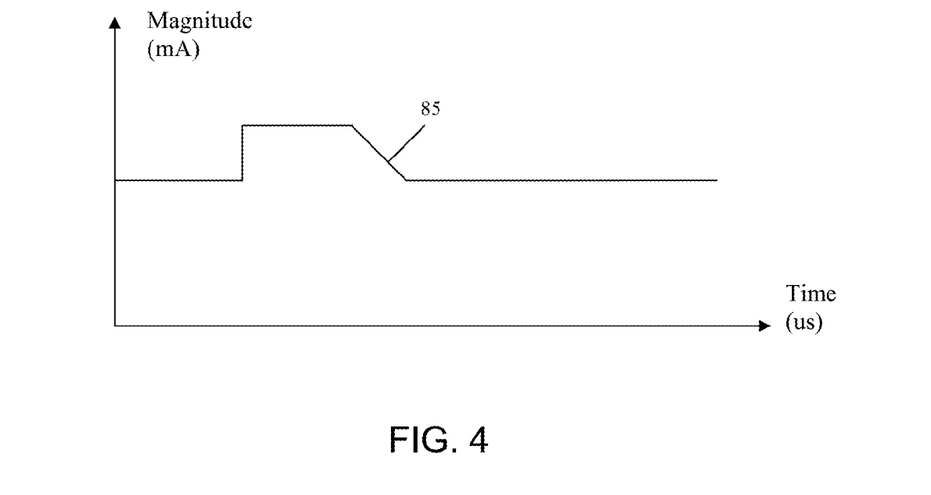
FIG. 4 is a diagram showing a stimulation pulse which may be applied by the needle localization system shown in FIG. 1.

(2) The stimulation current is maintained in magnitude and direction, but the stimulation waveform is changed so that its ending edge 85 is slowly decreasing to 0. The nerve responses are observed:

(a) If a nerve response is evoked, then the needle is not close enough to the nerve. The needle could be advanced further until a nerve response is not evoked.

(b) If a nerve response is not evoked, then the needle should be close enough to the nerve, and the needle position has been verified as ready for injection of the pharmacologically-active agent.

Furthermore, the present invention uses the relationships shown in FIG. 3 to provide an automated nerve locator. More particularly, in one preferred form of the present invention, needle localization system 5 preferably uses the following approach to provide an automated nerve locator:

(1) The needle is advanced while stimulating the nerve with a constant stimulation current flowing from anode to cathode (cathodic stimulation) and which has a rectangular pulse waveform. The magnitude of the current is noted as A1 in FIG. 3.

(2) When the nerve starts to activate, the position of the needle is crossing line 70 (i.e., the needle-nerve distance is less than X1 mm).

(3) Optionally, system 5 may switch the stimulation current direction so that it flows from cathode to anode (anodic stimulation). At this moment the nerve should not respond to the stimulation, so the stimulation is maintained at this level until the nerve responds again. At this time, the position of the needle should have crossed line 90 (i.e., the needle-nerve distance is less than X2 mm).

(4) Ending edge 85 of stimulation waveform is changed so that it slowly decreases to 0. The direction of the stimulation current is set so that it flows from anode to cathode (cathode stimulation). This stimulation current is maintained until the nerve does not respond. At this time, the position of the needle should have crossed line 75 (i.e., the needle-nerve distance is less than X3 mm).

(5) System 5 then advises the user (through the user interface) that the needle is in the proper position for injection of the pharmacologically-active agent.

Neuropathy Evaluation while Performing a Nerve Localization Procedure

As described above, in addition to stimulating a nerve, system 5 detects, processes and measures the nerve response signal when the system is used in a nerve localization procedure. By measuring the latency, the amplitude and/or other optional parameters of the nerve response signal, a neuropathy in the target nerve can be detected before advancing the needle further. This is a significant improvement over the prior art, and is made possible only because system 5 evokes, detects, processes and measures the nerve response signal. Further details regarding detection of neuropathies in the target nerve are disclosed in one or more of the following patents and patent applications (including the patents and patent applications referenced therein):

U.S. Pat. No. 5,851,191, issued Dec. 22, 1998 to Shai N. Gozani for APPARATUS AND METHODS FOR ASSESSMENT OF NEUROMUSCULAR FUNCTION;

U.S. Pat. No. 6,132,386, issued Oct. 17, 2000 to Shai N. Gozani et al. for METHODS FOR THE ASSESSMENT OF NEUROMUSCULAR FUNCTION BY F-WAVE LATENCY;

U.S. Pat. No. 6,266,558, issued Jul. 24, 2001 to Shai N. Gozani et al. for APPARATUS AND METHOD FOR NERVE CONDUCTION MEASUREMENTS WITH AUTOMATIC SETTING OF STIMULUS INTENSITY;

U.S. patent application Ser. No. 10/075,217, filed Feb. 14, 2002 by Shai N. Gozani et al. for APPARATUS AND METHOD FOR PERFORMING NERVE CONDUCTION STUDIES WITH LOCALIZATION OF EVOKED RESPONSES;

U.S. Pat. No. 7,493,157, issued Feb. 17, 2009 to Shai N. Gozani et al. for DEVICES AND METHODS FOR THE NON-INVASIVE DETECTION OF SPONTANEOUS MYOELECTRICAL ACTIVITY;

U.S. Pat. No. 7,452,335, issued Nov. 18, 2008 to Martin D. Wells et al. for METHOD AND APPARATUS FOR THE DETECTION OF NEUROMUSCULAR DISEASE USING DISEASE SPECIFIC EVOKED NEUROMUSCULAR RESPONSE ANALYSIS; and U.S. patent application Ser. No. 11/076,789, filed Mar. 9, 2005 by Shai N. Gozani et al. for METHOD FOR AUTOMATED DETECTION OF A-WAVES.

The foregoing patents and patent applications (including the patents and patent applications referenced therein) are hereby incorporated herein by reference.

Figure 5:
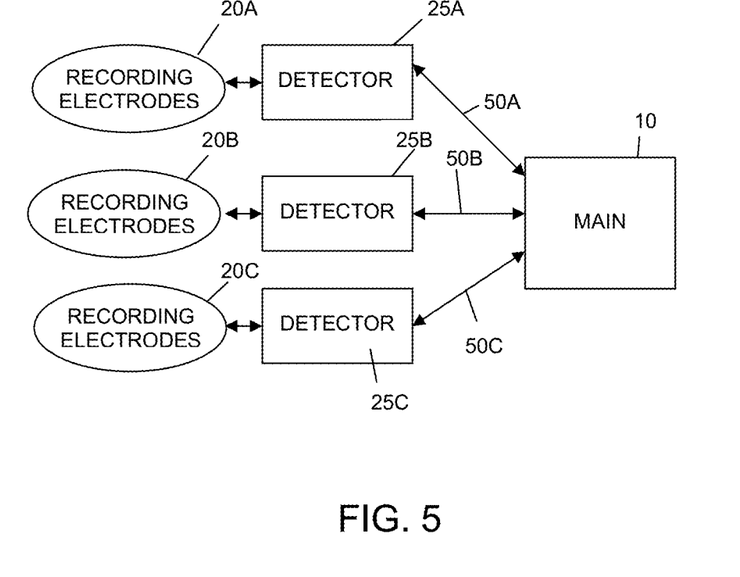
FIG. 5 is a schematic block diagram showing how multiple detector units may be used in conjunction with the present invention.

Multiple Detectors for Simultaneously Detecting Evoked Nerve Responses at Different Locations A user may wish to simultaneously detect nerve responses at multiple locations, e.g., to detect both motor nerve responses and sensory nerve responses, to detect the responses from different branches of the same nerve, etc. The present invention provides this feature. More particularly, main unit 10 is configured so that it can be connected to, and use the inputs from, multiple detector units 25A, 25B, 25C, etc., whereby to acquire signals from electrodes 20A, 20B, 20C, etc., as shown in FIG. 5. The connections between any detector unit 25 and main unit 10 can be wired or wireless. This allows system 5 to detect, process and measure nerve responses from multiple locations simultaneously. As an option, instead of using multiple detector units 25A, 25B, 25C, etc. that are configured with only one channel each (i.e., for connection to a single pair of electrodes 20 which include an active electrode and a passive electrode), a detector unit 25 can be used that is configured with multiple channels (i.e., for connection to multiple pairs of electrodes 20). These multiple pairs of electrodes may share a common passive electrode.

Wireless Connection Between The Main Unit And A Detector Unit

A wireless connection 50 between main unit 10 and detector unit 25 (or detector units 25A, 25B, 25C, etc.) allows the detector unit to detect the nerve response signal without requiring a cable to be used to connect detector unit 25 and main unit 10 (which would be the case if the connection were not wireless).

If desired, a wireless connection 50 between main unit 10 and a detector unit 25 can be implemented by using a wireless module such as Bluetooth or other RF transceiver. Other wireless means such as optical units comprising infrared wavelengths can also be used. To this end, a wireless module 95 is preferably included in main unit 10, and a wireless module 100 is preferably included in each detector unit 25. Once wireless module 95 in main unit 10 and the wireless modules 100 in detector units 25 establish wireless connection, main unit 10 can check the status of the various detector units 25, set the gain of Analog Front End (AFE) 105 (which transmits data to the detector controller 120 through an analog-to-digital converter ADC 107), set waveform acquisition parameters, obtain the waveform data from the detector units, etc.

In order to measure the latency of the nerve response signal, which is the time period from stimulation onset to the start of the response waveform, and which can be important for certain purposes (e.g., neuropathy evaluation) it is important to synchronize the stimulation and data acquisition so that the time period between the stimulation and the start of the data acquisition is a known value. To this end, it is preferred that main unit 10 sends a signal to detector unit(s) 25 to start the data acquisition. Such a signal may be referred to as a "Synchronization Signal". In the present invention, when main unit 10 and detector unit(s) 25 are connected wirelessly, the synchronization between the stimulation and the data acquisition is preferably implemented as an RF signal (although a wireless optical signal can also be implemented). In one preferred form of the present invention, needle localization system 5 preferably uses the following approach to provide synchronization between the stimulation and the data acquisition:

(1) An RF transmitter 110 in main unit 10 transmits a Synchronization Signal, which is preferably an RF signal modulated with a modulation signal. The modulation signal may be a digital signal with a pre-defined bit combination, e.g., 11010110.

(2) An RF receiver 115 in detector unit 25 receives the Synchronization Signal sent from main unit 10, and detects the modulation signal of the RF signal.

(3) If the detected modulation signal has the pre-defined bit combination, e.g., 11010110, then it is interpreted as a valid Synchronization Signal. Detector unit 25 may send a message to main unit 10 to acknowledge that it receives a valid Synchronization Signal. Detector unit 25 will start the data acquisition. The detector controller 120 records the time when the detected modulation signal arrives. The duration from the time the modulation signal is detected to the time the data acquisition starts will be sent to main unit 10.

(4) If the detected modulation signal does not match the pre-defined bit combination, e.g., 11010110, then it is not a valid Synchronization Signal and the detector unit will not start the data acquisition. The detector unit may send a message to main unit 10 when it receives an invalid Synchronization Signal. Main unit 10 may then repeat the process again from Step 1 above until synchronization is successful or until the system times out.

If desired, wireless module 95 may be used as the RF transmitter so that RF transmitter 110 can be eliminated.

Furthermore, if desired, wireless module 100 may be used as the RF receiver so that RF receiver 115 can be eliminated.

Data Logging And Outcome Tracking

Main unit 10 of the present invention records the data and outcome of the stimulator-guided nerve localization procedure for both clinical and medicolegal purposes. The information recorded in main unit 10 may include but is not limit to:

(1) patient information entered by the user;
(2) physician information entered by the user;
(3) clinical information entered by the user, including but not limited to:
  (a) the procedure;
  (b) the target nerve;
  (c) the stimulation position; and
  (d) the detection position;
(4) stimulation parameters for each stimulus;
(5) detected nerve response waveforms and measurements; and
(6) the outcome of the nerve localization—"successful" or "failed".

Transmission of Data to Data Server

The data recorded by system 5 can be transferred to a hub 125. The connection 130 between hub 125 and main unit 10 can be wired or wireless. Hub 125 receives the data and preferably transfers it to a central data storage 135 via telephone line or Internet or other transmission medium for data storage and report generation.

Application of the Present Invention to Medical Instruments or Devices Other than Needles In the foregoing description, the present invention is discussed in the context of localizing a needle to a nerve. However, it should be appreciated that it may sometimes be desirable to localize other medical instruments or devices to a nerve, e.g., a probe, a sensor, a tissue separator, a cutting device, a biopsy device, a suturing device, a stapling device, an implant, etc. The present invention may be used to localize any of these instruments or devices, or other instruments or devices, to a nerve.

Modifications

While the foregoing invention has been described with reference to its preferred embodiments, various alterations and modifications will occur to those skilled in the art in view of the present disclosure. All such alterations and modifications are intended to fall within the scope of the invention.

What is claimed is:

1. A method for localizing a needle to a nerve, the method comprising:
    inserting the needle into a patient;
    using the inserted needle to electrically stimulate the nerve, with a known current intensity, so as to evoke a nerve response;
    electronically detecting the nerve response through an electrode placed on the patient;
    analyzing the electronically detected nerve response so as to identify at least one attribute of the same;
    confirming that the inserted needle is in the immediate proximity of the nerve based upon known current intensity and at least one identified attribute of the electronically detected nerve response; and
    detecting neuropathies in the nerve based upon at least one identified attribute of the detected nerve response.

2. A method according to claim 1 wherein the confirmed immediate proximity of the inserted needle to the nerve is such that injection of a pharmacologically-active agent is clinically effective.

3. A method according to claim 1 wherein the needle is a hypodermic needle.

4. A method according to claim 1 wherein the needle is a hypodermic needle that is electrically insulated up to its tip.

5. A method according to claim 1 wherein the nerve is electrically stimulated using the inserted needle and a surface electrode.

6. A method according to claim 1 wherein the nerve is electrically stimulated using a bi-polar needle.

7. A method according to claim 1 wherein the at least one identified attribute used to predict the proximity of the inserted needle to the nerve comprises the amplitude of the nerve response.

8. A method according to claim 7 wherein the nerve response is rectified prior to measurement of the amplitude.

9. A method according to claim 1 wherein the at least one identified attribute used to predict the proximity of the inserted needle to the nerve comprises the threshold response of the nerve to a specified amplitude.

10. A method according to claim 9 wherein the immediate proximity of the inserted needle to the nerve is confirmed by a threshold nerve response at a stimulation current in a pre-determined range.

11. A method according to claim 10 wherein the pre-determined stimulation current range is 0.2 to 0.5 mA.

12. A method according to claim 11 wherein the pre-determined stimulation current range is based on a 100 μsec stimulation pulse duration.

13. A method according to claim 11 wherein the lowest stimulation current within the pre-determined stimulation current range is determined.

14. A method according to claim 13 wherein the said lowest stimulation current is automatically determined based on at least one identified nerve response attribute.

15. A method according to claim 10 wherein the pre-determined stimulation current range is modified if the test subject is determined to have a neuropathy.

16. A method according to claim 15 wherein said current modification is performed automatically based on at least one identified nerve response attribute.

17. A method according to claim 1 wherein the intensity of the electrical stimulus applied to the test subject is automatically controlled in accordance with at least one identified attribute of the desired nerve response.

18. A method according to claim 1 wherein the intensity of the electrical stimulus applied to the test subject is automatically controlled by:
  (1) delivering an electrical stimulus to the nerve, and detecting and analyzing the nerve response;
  (2) if the amplitude of the nerve response exceeds a pre-determined threshold, decreasing the intensity of the electrical stimulus;
  (3) if the amplitude of the nerve response is below a pre-determined threshold, increasing the intensity of the electrical stimulus;
  (4) repeating steps 1-3 until the changes in the intensity of the electrical stimulus are smaller than a pre-determined range;
  (5) if the intensity of the electrical stimulus is higher than a target current range, alerting a user that the inserted needle is not in the immediate vicinity of the nerve; and
  (6) if the intensity of the electrical stimulus is within a target current range, alerting a user that the inserted needle is in the immediate vicinity of the nerve; and
  (7) if the intensity of the electrical stimulus is below a target current range, alerting a user that the inserted needle may be in physical contact with the nerve.

19. A method according to claim 18 wherein the pre-determined range in step (4) is 0.1 mA.

20. A method according to claim 18 wherein the electrical stimulus has a repetition rate of 1 Hz.

21. A method according to claim 18 wherein the electrical stimulus has a repetition rate in the range of 2 Hz.

22. A method according to claim 18 wherein the target current is approximately 0.2 mA to approximately 0.5 mA.

23. A method according to claim 1 wherein the at least one identified attribute used to detect neuropathy in the nerve comprises the amplitude of the nerve response.

24. A method according to claim 1 wherein the at least one identified attribute used to detect neuropathy in the nerve comprises the time delay between the application of the electrical stimulus to a subject and the detection of the nerve response onset.

25. A method according to claim 1 wherein a nerve response is detected at a single location.

26. A method according to claim 1 wherein nerve responses are detected at a plurality of locations.

27. A method according to claim 26 wherein the detection of the nerve responses at a plurality of locations is synchronized.

28. A method according to claim 1 wherein at least one of the detected nerve responses and the at least one identified attribute of the detected nerve response is logged.

29. A method according to claim 28 wherein the stimulation current intensity is also logged.

30. A method according to claim 1 wherein at least one of the detected nerve response and the at least one identified attribute of the detected nerve response is stored.

31. A method according to claim 30 wherein the stimulation current intensity is also stored.

32. A method according to claim 30 wherein storage occurs at a remote site.

33. Apparatus for localizing a needle to a nerve of a patient, the apparatus comprising:
  an electrical stimulator connected to the needle for electrically stimulating the nerve, with a known current intensity, after the needle has been inserted into the patient so as to evoke a nerve response;
  at least one sensor placed on the patient for electronically detecting the nerve response;
  an analysis unit connected to the sensor for receiving the electronically detected nerve response and identifying at least one attribute of the same;
  a localizing unit connected to the analysis unit for confirming that the inserted needle is in the immediate proximity of the nerve based upon known current intensity and at least one identified attribute of the electronically detected nerve response; and
  a neuropathy detection unit for detecting neuropathies in the nerve based upon at least one identified attribute of the detected nerve response.

34. Apparatus according to claim 33 wherein the confirmed immediate proximity of the inserted needle to the nerve is such that injection of a pharmacologically-active agent is clinically effective.

35. Apparatus according to claim 33 wherein the needle is a hypodermic needle.

36. Apparatus according to claim 33 wherein the at least one identified attribute used to predict the proximity of the inserted needle to the nerve comprises the amplitude of the nerve response.

37. Apparatus according to claim 33 wherein the at least one identified attribute used to predict the proximity of the inserted needle to the nerve comprises the threshold response of the nerve to a specified amplitude.

38. Apparatus according to claim 37 wherein the immediate proximity of the inserted needle to the nerve is confirmed by a threshold nerve response at a stimulation current in a pre-determined range.

39. Apparatus according to claim 38 wherein the pre-determined stimulation current range is 0.2 to 0.5 mA.

40. Apparatus according to claim 39 wherein the pre-determined stimulation current range is based on a 100 μsec stimulation pulse duration.

41. Apparatus according to claim 39 wherein the lowest stimulation current within the pre-determined stimulation current range is determined.

42. Apparatus according to claim 41 wherein the lowest stimulation current is automatically determined based on at least one identified nerve response attribute.

43. Apparatus according to claim 38 wherein the pre-determined stimulation current range is modified if the test subject is determined to have a neuropathy.

44. Apparatus according to claim 43 wherein said current modification is performed automatically based on at least one identified nerve response attribute.

45. Apparatus according to claim 33 wherein the intensity of the electrical stimulus applied to the test subject is automatically controlled in accordance with at least one identified attribute of the desired nerve response.

46. Apparatus according to claim 33 wherein the apparatus is configured so that the intensity of the electrical stimulus applied to the test subject is automatically controlled by:
   (1) delivering an electrical stimulus to the nerve, and detecting and analyzing the nerve response;
   (2) if the amplitude of the nerve response exceeds a pre-determined threshold, decreasing the intensity of the electrical stimulus;
   (3) if the amplitude of the nerve response is below a pre-determined threshold, increasing the intensity of the electrical stimulus;
   (4) repeating steps 1-3 until the changes in the intensity of the electrical stimulus are smaller than a pre-determined range;
   (5) if the intensity of the electrical stimulus is higher than a target current range, alerting a user that the inserted needle is not in the immediate vicinity of the nerve; and
   (6) if the intensity of the electrical stimulus is within a target current range, alerting a user that the inserted needle is in the immediate vicinity of the nerve; and
   (7) if the intensity of the electrical stimulus is below a target current range, alerting a user that the inserted needle may be in physical contact with the nerve.

47. Apparatus according to claim 46 wherein the pre-determined range in step (4) is 0.1 mA.

48. Apparatus according to claim 46 wherein the electrical stimulus has a repetition rate of 1 Hz.

49. Apparatus according to claim 46 wherein the electrical stimulus has a repetition rate in the range of 2 Hz.

50. Apparatus according to claim 46 wherein the target current is approximately 0.2 mA to approximately 0.5 mA.

51. Apparatus according to claim 33 wherein the at least one identified attribute used to detect neuropathy in the nerve comprises the amplitude of the nerve response.

52. Apparatus according to claim 33 wherein the at least one identified attribute used to detect neuropathy in the nerve comprises the time delay between the application of the electrical stimulus to a subject and the detection of the nerve response onset.

53. Apparatus according to claim 33 wherein a nerve response is detected at a single location.

54. Apparatus according to claim 33 wherein nerve responses are detected at a plurality of locations.

55. Apparatus according to claim 54 wherein the detection of the nerve responses at a plurality of locations is synchronized.

56. Apparatus according to claim 33 wherein at least one of the detected nerve responses and the at least one identified attribute of the detected nerve response is logged.

57. Apparatus according to claim 56 wherein the stimulation current intensity is also logged.

58. Apparatus according to claim 33 wherein at least one of the detected nerve response and the at least one identified attribute of the detected nerve response is stored.

59. Apparatus according to claim 58 wherein the stimulation current intensity is also stored.

60. A method according to claim 58 wherein storage occurs at a remote site.

61. A method for localizing a needle to a nerve, the method comprising:
   using the needle to electrically stimulate the nerve, with a known current intensity, so as to evoke a nerve response;
   detecting the nerve response;
   analyzing the detected nerve response so as to identify at least one attribute of the same; and
   confirming that the needle is in the immediate proximity of the nerve based upon known current intensity and at least one identified attribute of the detected nerve response;
   wherein the at least one identified attribute used to predict the proximity of the needle to the nerve comprises the threshold response of the nerve to a specified amplitude;
   wherein the immediate proximity of needle to nerve is confirmed by a threshold nerve response at a stimulation current in a pre-determined range; and
   wherein the pre-determined stimulation current range is modified if the test subject is determined to have a neuropathy.

62. A method according to claim 61 wherein said current modification is performed automatically based on at least one identified nerve response attribute.

63. A method for localizing a needle to a nerve, the method comprising:
   using the needle to electrically stimulate the nerve, with a known current intensity, so as to evoke a nerve response;
   detecting the nerve response;
   analyzing the detected nerve response so as to identify at least one attribute of the same; and
   confirming that the needle is in the immediate proximity of the nerve based upon known current intensity and at least one identified attribute of the detected nerve response;
   wherein the intensity of the electrical stimulus applied to the test subject is automatically controlled by:
   (1) delivering an electrical stimulus to the nerve, and detecting and analyzing the nerve response;
   (2) if the amplitude of the nerve response exceeds a pre-determined threshold, decreasing the intensity of the electrical stimulus;
   (3) if the amplitude of the nerve response is below a pre-determined threshold, increasing the intensity of the electrical stimulus;
   (4) repeating steps 1-3 until the changes in the intensity of the electrical stimulus are smaller than a pre-determined range;
   (5) if the intensity of the electrical stimulus is higher than a target current range, alerting a user that the needle is not in the immediate vicinity of the nerve; and
   (6) if the intensity of the electrical stimulus is within a target current range, alerting a user that the needle is in the immediate vicinity of the nerve; and
   (7) if the intensity of the electrical stimulus is below a target current range, alerting a user that the needle may be in physical contact with the nerve.

64. A method according to claim 63 wherein the pre-determined range in step (4) is 0.1 mA.

65. A method according to claim 63 wherein the electrical stimulus has a repetition rate of 1 Hz.

66. A method according to claim 63 wherein the electrical stimulus has a repetition rate in the range of 2 Hz.

67. A method according to claim 63 wherein the target current is approximately 0.2 mA to approximately 0.5 mA.

68. A method for localizing a needle to a nerve, the method comprising:
  using the needle to electrically stimulate the nerve, with a known current intensity, so as to evoke a nerve response;
  detecting the nerve response;
  analyzing the detected nerve response so as to identify at least one attribute of the same;
  confirming that the needle is in the immediate proximity of the nerve based upon known current intensity and at least one identified attribute of the detected nerve response; and
  detecting neuropathies in the nerve based upon at least one identified attribute of the detected nerve response.

69. A method according to claim 68 wherein the at least one identified attribute used to detect neuropathy in the nerve comprises the amplitude of the nerve response.

70. A method according to claim 68 wherein the at least one identified attribute used to detect neuropathy in the nerve comprises the time delay between the application of the electrical stimulus to a subject and the detection of the nerve response onset.

71. Apparatus for localizing a needle to a nerve, the apparatus comprising:
  an electrical stimulator connected to the needle for electrically stimulating the nerve, with a known current intensity, so as to evoke a nerve response;
  at least one sensor for detecting the nerve response;
  an analysis unit connected to the sensor for receiving the detected nerve response and identifying at least one attribute of the same; and
  a localizing unit connected to the analysis unit for confirming that the needle is in the immediate proximity of the nerve based upon known current intensity and at least one identified attribute of the detected nerve response;
  wherein the at least one identified attribute used to predict the proximity of the needle to the nerve comprises the threshold response of the nerve to a specified amplitude;
  wherein the immediate proximity of needle to nerve is confirmed by a threshold nerve response at a stimulation current in a pre-determined range; and
  wherein the pre-determined stimulation current range is modified if the test subject is determined to have a neuropathy.

72. Apparatus according to claim 71 wherein said current modification is performed automatically based on at least one identified nerve response attribute.

73. Apparatus for localizing a needle to a nerve, the apparatus comprising:
  an electrical stimulator connected to the needle for electrically stimulating the nerve, with a known current intensity, so as to evoke a nerve response;
  at least one sensor for detecting the nerve response;
  an analysis unit connected to the sensor for receiving the detected nerve response and identifying at least one attribute of the same; and
  a localizing unit connected to the analysis unit for confirming that the needle is in the immediate proximity of the nerve based upon known current intensity and at least one identified attribute of the detected nerve response;
  wherein the apparatus is configured so that the intensity of the electrical stimulus applied to the test subject is automatically controlled by:
  (1) delivering an electrical stimulus to the nerve, and detecting and analyzing the nerve response;
  (2) if the amplitude of the nerve response exceeds a pre-determined threshold, decreasing the intensity of the electrical stimulus;
  (3) if the amplitude of the nerve response is below a pre-determined threshold, increasing the intensity of the electrical stimulus;
  (4) repeating steps 1-3 until the changes in the intensity of the electrical stimulus are smaller than a pre-determined range;
  (5) if the intensity of the electrical stimulus is higher than a target current range, alerting a user that the needle is not in the immediate vicinity of the nerve; and
  (6) if the intensity of the electrical stimulus is within a target current range, alerting a user that the needle is in the immediate vicinity of the nerve; and
  (7) if the intensity of the electrical stimulus is below a target current range, alerting a user that the needle may be in physical contact with the nerve.

74. Apparatus according to claim 73 wherein the pre-determined range in step (4) is 0.1 mA.

75. Apparatus according to claim 73 wherein the electrical stimulus has a repetition rate of 1 Hz.

76. Apparatus according to claim 73 wherein the electrical stimulus has a repetition rate in the range of 2 Hz.

77. Apparatus according to claim 73 wherein the target current is approximately 0.2 mA to approximately 0.5 mA.

78. Apparatus for localizing a needle to a nerve, the apparatus comprising:
  an electrical stimulator connected to the needle for electrically stimulating the nerve, with a known current intensity, so as to evoke a nerve response;
  at least one sensor for detecting the nerve response;
  an analysis unit connected to the sensor for receiving the detected nerve response and identifying at least one attribute of the same;
  a localizing unit connected to the analysis unit for confirming that the needle is in the immediate proximity of the nerve based upon known current intensity and at least one identified attribute of the detected nerve response; and
  a neuropathy detection unit for detecting neuropathies in the nerve based upon at least one identified attribute of the detected nerve response.

79. Apparatus according to claim 78 wherein the at least one identified attribute used to detect neuropathy in the nerve comprises the amplitude of the nerve response.

80. Apparatus according to claim 78 wherein the at least one identified attribute used to detect neuropathy in the nerve comprises the time delay between the application of the electrical stimulus to a subject and the detection of the nerve response onset.

81. A method for localizing a needle to a nerve of a patient and verifying that the needle is close to the nerve of the patient, the method comprising:
  inserting the needle into the patient;
  advancing the needle toward the nerve while stimulating the nerve with the stimulation current flowing from anode to cathode and having a rectangular pulse waveform;
  switching the stimulation current flow direction from anode to cathode to cathode to anode while maintaining the stimulation current intensity and then further advancing the needle toward the nerve until a nerve response is evoked;
  altering the stimulation current pulse waveform to a stimulation current pulse waveform with a sharp rising edge and a slowly decaying falling edge, switching the stimulation current flow direction from cathode to anode to anode to cathode, and further advancing the needle until a nerve response is no longer evoked; and alerting a user that the needle is close to the nerve of the patient.

82. A method for localizing a needle to a nerve of a patient and verifying that the needle is close to the nerve of the patient, the method comprising:
- inserting the needle into the patient;
- stimulating the nerve until a nerve response is evoked, with the stimulation current flowing from anode to cathode and having a rectangular pulse waveform;
- advancing the needle toward the nerve while gradually reducing the stimulation current intensity to a target current intensity and while continuing to detect an evoked nerve response;
- after the stimulation current intensity is reduced to or lower than the target current intensity while still detecting an evoked nerve response, altering the stimulation current pulse waveform from a rectangular pulse waveform to a stimulation current pulse waveform having a sharp rising edge and a slowly decaying falling edge;
- further advancing the needle toward the nerve so long as a nerve response is evoked with the stimulation current intensity at or lower than the target current intensity; and
- once a nerve response is no longer evoked with the stimulation current intensity at or lower than the target current intensity, alerting a user that the needle is close to the nerve of the patient.

83. The method according to claim 82 wherein the target current intensity is approximately 0.2 mA to approximately 0.5 mA.

* * * * *